(12) United States Patent
Angst et al.

(10) Patent No.: US 12,332,233 B2
(45) Date of Patent: Jun. 17, 2025

(54) SENSOR ASSEMBLY FOR DETERMINING PROPERTIES OF A CONCRETE STRUCTURE AND CONCRETE STRUCTURE

(71) Applicant: ETH Zurich, Zurich (CH)

(72) Inventors: Ueli Angst, Wuerenlos (CH); Yurena Segui Femenias, Zurich (CH)

(73) Assignee: ETH ZURICH, Zurich (CH)

( * ) Notice: Subject to any disclaimer, the term of this patent is extended or adjusted under 35 U.S.C. 154(b) by 233 days.

(21) Appl. No.: 17/946,860

(22) Filed: Sep. 16, 2022

(65) Prior Publication Data
US 2023/0015155 A1 Jan. 19, 2023

Related U.S. Application Data

(63) Continuation of application No. PCT/EP2021/056448, filed on Mar. 15, 2021.

(30) Foreign Application Priority Data

Mar. 17, 2020 (EP) .................................... 20163527

(51) Int. Cl.
*G01L 1/16* (2006.01)
*G01N 17/00* (2006.01)
*G01N 33/38* (2006.01)

(52) U.S. Cl.
CPC .............. *G01N 33/383* (2013.01); *G01L 1/16* (2013.01); *G01N 17/00* (2013.01)

(58) Field of Classification Search
CPC ......... G01N 33/383; G01N 17/00; G01L 1/16
See application file for complete search history.

(56) References Cited

U.S. PATENT DOCUMENTS

| 6,796,187 B2 | 9/2004 | Srinivasan et al. |
| 7,034,660 B2 * | 4/2006 | Watters ............... G01M 5/0008 |
| | | 205/777 |
| 7,804,406 B2 | 9/2010 | Kaga et al. |
| | (Continued) | |

FOREIGN PATENT DOCUMENTS

| CN | 202166404 U | 3/2012 |
| CN | 102384803 B | 12/2012 |
| | (Continued) | |

OTHER PUBLICATIONS

International Search Report dated Apr. 9, 2021 in corresponding application PCT/EP2021/056448.
(Continued)

Primary Examiner — Jamel E Williams
(74) Attorney, Agent, or Firm — Muncy, Geissler, Olds & Lowe, P.C.

(57) ABSTRACT

A sensor assembly adapted to be embedded in a concrete structure comprising a body, and at least one sensor configured to determine parameters related to the durability of a concrete structure, wherein the sensor is arranged at least partially within the body, wherein the body comprises a shell covering the outer surface of the body and consisting of or comprising a mineral material, and wherein the sensor assembly has a rounded shape, particularly an ellipsoid or spherical shape, and a first extension extending along a first axis being 90 mm or less. A concrete structure is also provided having at least one sensor assembly.

14 Claims, 2 Drawing Sheets

(56) References Cited

U.S. PATENT DOCUMENTS

| | | | |
|---|---|---|---|
| 10,324,078 B2 | 6/2019 | Ghods et al. | |
| 11,156,593 B2 | 10/2021 | Ghods et al. | |
| 2015/0048844 A1* | 2/2015 | Neikirk | G01N 27/021 |
| | | | 324/682 |
| 2018/0340925 A1* | 11/2018 | Radjy | G01N 27/121 |

FOREIGN PATENT DOCUMENTS

| | | | |
|---|---|---|---|
| CN | 103675030 B | 8/2016 | |
| CN | 106226506 A | 12/2016 | |
| CN | 106383060 A | 2/2017 | |
| CN | 106441074 A | 2/2017 | |
| CN | 106787944 A | 5/2017 | |
| CN | 107024579 A | 8/2017 | |
| CN | 207318399 U | 5/2018 | |
| CN | 208238992 U | 12/2018 | |
| DE | 102009040942 A1 | 3/2011 | |
| EP | 1909218 A1 | 4/2008 | |
| EP | 3236258 A2 | 10/2017 | |
| KR | 20120029303 A | 3/2012 | |
| KR | 101926979 B1 | 12/2018 | |
| WO | WO0246701 A2 | 6/2002 | |
| WO | WO03006958 A1 | 1/2003 | |
| WO | WO-2004046704 A1 * | 6/2004 | G01N 33/383 |
| WO | WO-2010146726 A1 * | 12/2010 | G01B 7/16 |
| WO | WO2011043442 A1 | 4/2011 | |

OTHER PUBLICATIONS

Shaoyu Zhao et al; "A spherical smark aggregate sensor based electro-mechanical impedance method for quantitative damage evaluation of concrete" Dec. 2, 2019 pp. 1560-1576.

* cited by examiner

SENSOR ASSEMBLY FOR DETERMINING PROPERTIES OF A CONCRETE STRUCTURE AND CONCRETE STRUCTURE

This nonprovisional application is a continuation of International Application No. PCT/EP2021/056448, which was filed on Mar. 15, 2021, and which claims priority to European Patent Application No. 20 163 527.3, which was filed in Europe on Mar. 17, 2020, and which are both herein incorporated by reference.

BACKGROUND OF THE INVENTION

Field of the Invention

The present invention relates to a sensor assembly for determining parameters related to the durability of a concrete structure and a concrete structure comprising at least one sensor assembly embedded in the concrete structure.

Description of the Background Art

Corrosion of steel reinforcements is one of the most widespread degradation mechanisms in reinforced concrete structures. In addition to loss in serviceability and safety, corrosion causes high costs to all industrialized countries. The use of embedded sensors allows obtaining continuous information on the condition of the structure; thus, it allows detecting damage and critical conditions in due time. This permits refining maintenance planning and optimization of concrete repairs. As a consequence, structures can be used safely for longer times, thus reducing the costs.

A variety of sensors for monitoring the parameters associated with durability of reinforced concrete (potential, moisture, temperature, resistivity, galvanic current, etc.) are available.

However, the current monitoring systems are usually bulky and have very different material and geometrical properties compared to the concrete components (cement paste, aggregates). Both the shape and materials (mostly plastic materials) of the sensors according to the prior art are completely different from any constituents of concrete (aggregates, cement-based materials), thus introducing artefacts exactly at the location of the measurement.

The presence of foreign bodies, e.g. sensors and spacers, embedded in concrete impose significant differences in concrete properties at the interface between the foreign body and the concrete compared to the bulk concrete.

For example, a modified microstructure at the concrete cover could be demonstrated in the presence of spacers, i.e., devices used to secure the position of the reinforcing steel bar against formwork during concrete casting. In one exemplary experiment (S. Alzyoud, H. S. Wong, N. R. Buenfeld (2016), Influence of reinforcement spacers on mass transport properties and durability of concrete structures, Cement and Concrete Research, 87, 31-44), a plastic clip-on "A" spacer to achieve 50 mm cover depth changed dramatically the concrete microstructure in its vicinity.

These changes in microstructural features of the concrete locally influence the transport processes through the concrete. For instance, it was reported that spacers can facilitate ingress of aggressive agents (water, chloride ions, $CO_2$, and oxygen) through the spacer itself or its interface with concrete (S. Alzyoud, H. S. Wong, N. R. Buenfeld (2016), Influence of reinforcement spacers on mass transport properties and durability of concrete structures, Cement and Concrete Research, 87, 31-44).

As an example of this, the distribution of chlorides in concrete samples that were exposed to chloride ingress at the area of the spacer location could be demonstrated (S. Alzyoud, H. S. Wong, N. R. Buenfeld (2016), Influence of reinforcement spacers on mass transport properties and durability of concrete structures, Cement and Concrete Research, 87, 31-44).

Different types of spacers were also tested (S. Alzyoud, H. S. Wong, N. R. Buenfeld (2016), Influence of reinforcement spacers on mass transport properties and durability of concrete structures, Cement and Concrete Research, 87, 31-44; S. Alzyoud (2015), Effect of reinforcement spacers on concrete microstructure and durability, PhD thesis, Imperial College London). These had different geometries and were made, in addition to plastic, of cementitious materials and steel. The results showed in all cases that spacers increase mass transport. This is because the spacer-concrete interface contains higher porosity, lower cement content, and therefore higher water/binder ratio compared to the concrete farther away from the spacer.

It can be concluded that if sensors embedded in concrete have geometries different from the components typically found in concrete, as for example electrodes according to the prior art, this will affect the compaction of the concrete, which will in turn modify the concrete microstructure and transport properties.

Additionally, it was shown that the presence of foreign bodies made out of steel or plastic and embedded in the concrete also significantly modifies the moisture transport through the concrete compared to cementitious spacers; consequently, the materials used for the construction of embedded sensors in concrete, which are usually plastic and metallic materials, may absorb moisture in a very different manner than mineral materials (e.g. aggregates or cement paste), influencing the moisture transport, which is known to play an important role in the corrosion rate in reinforced concrete (L. Bertolini, B. Elsener, P. Pedeferri, E. Redaelli; R. P. Polder (2013), Corrosion of steel in concrete, second ed., Wiley, Weinheim).

SUMMARY OF THE INVENTION

It is therefore essential to improve the geometry and composition of the embedded sensors in concrete, as the available systems act as weak links and accelerate ingress of aggressive agents and will lead to results that are not representative of the bulk concrete.

Thus, the objective problem underlying the present invention is to provide a sensor assembly for determining the parameters related to the durability of a concrete structure which is improved in view of the above-discussed disadvantages of the prior art, in particular a sensor assembly which does not modify the determined parameters due to the presence of the sensor itself, i.e. without introduction of microstructural features and other artefacts influencing the transport of harmful species through the concrete in the surroundings of the sensor itself.

A first aspect of the invention relates to a sensor assembly (also referred to herein as a 'smart aggregate') for determining parameters related to the durability of a reinforced or unreinforced concrete structure, wherein the sensor assembly comprises a body and at least one sensor, the at least one sensor being configured to determine parameters related to the durability of a concrete structure when the sensor assembly is embedded in the concrete structure, wherein the sensor is arranged at least partially within the body.

The body comprises a shell covering the outer surface of the body, wherein said shell consists of or comprises a mineral material, wherein particularly the material of the shell consists of or is formed substantially of at least 90% (weight by weight) mineral material.

Furthermore, the sensor assembly, particularly the shell, has a rounded shape, particularly an ellipsoid or spherical shape, wherein the sensor assembly comprises a first extension, particularly a height, extending along a first axis, and wherein the first extension is 90 mm or less.

The sensor assembly, particularly the shell, can comprise a second extension, particularly a width, extending along a second axis perpendicular to the first axis, wherein a ratio between the first extension and the second extension is 1:3 to 3:1. Thereby, the ratio between the first extension and the second extension is in the same range as for concrete aggregates, and additionally, good compaction within the concrete body, is assured.

The term 'concrete structure' as used herein may refer to any structure comprising reinforced or unreinforced concrete, e.g., concrete infrastructure such as bridges or tunnels, buildings, or laboratory and field testing specimens. A concrete structure typically comprises a hardened mortar or cement paste containing mineral aggregates disposed therein. The sensor assembly is embedded in the concrete structure, in other words arranged inside of the concrete structure, i.e., completely covered by the concrete structure on all sides.

The determined parameters of the concrete structure particularly relate to durability monitoring (e.g., corrosion monitoring) and/or structural health monitoring (e.g. monitoring of mechanical strains and stresses).

The body and the shell covering the body may be formed from different materials or from the same material. In the latter case, the shell is particularly integrally formed with the body. In particular, the body comprises at least one cavity for arranging components of the sensor assembly, such as sensors, electronic circuitry, a microcontroller, an energy source (e.g., a battery), or a wireless communication module.

In the context of the present specification, the 'mineral material' is produced from the reaction of a mineral binder with water. Mineral binders can be obtained from stones, rocks, or as a product of a technical manufacturing process. By definition, when a mineral binder is mixed with water, certain chemical reactions occur, which lead to a development of strength over time. Mineral binders are used in making mortars, concrete, plasters, and other important materials for construction. Thus, in particular, this definition excludes plastic, rubber as well as other organic materials and metals, which are commonly contained in sensors according to the prior art for determining concrete durability and structural health. Thus, artifacts introduced into the concrete structure by such materials are advantageously avoided due to the mineral material of the shell of the sensor assembly according to the present invention.

According to the invention, the sensor assembly can have a rounded shape, meaning that, just like concrete aggregates, the sensor assembly lacks sharp corners and edges which adversely affect the local composition of the concrete structure.

The absolute first extension and the first extension/second extension ratio of the sensor assembly is particularly in the same range as for concrete aggregates, ensuring that the sensor assembly does not adversely affect the local composition of the concrete structure. In addition, good compaction within the concrete body is assured.

Advantageously, due to the material composition of the shell and due to its shape and size, the sensor assembly resembles a concrete aggregate and does not (or to a very small extent) introduce artifacts that lead to changes in the microstructure and transport processes in the concrete structure. The sensor assembly thus allows to capture the real behavior of durability and/or structural health processes occurring in concrete.

Further, the geometry of the sensor assembly can be in agreement with the requirements for concrete aggregates in applicable standards, for example European Standard EN 12620 (Aggregates for concrete).

The shell of the sensor assembly can comprise a sensor surface formed by the at least one sensor, wherein the sensor surface is disposed on the outside surface of the sensor assembly, such that the sensor surface is configured to contact the concrete structure (in particular the cement paste or mortar) adjacent the sensor assembly when the sensor assembly is embedded in the concrete structure. The sensor surface an be formed by the part or parts of the sensor or plurality of sensors which is/are arranged at the surface of the shell.

In case of one sensor, the sensor surface can be comprised in the single sensor, and in case of more than one sensor, the sensor surface can be jointly formed by the plurality of sensors. The sensor surface may comprise any shape and may be formed from any material, not only mineral materials. In addition, the sensor surface may or may not protrude from the outer surface of the shell. In particular, in case of a plurality of sensors forming the sensor surface, the sensor surface is discontinuous, i.e. formed by a plurality of partial surfaces separated from each other, particularly separated by mineral material of the shell.

The surface area of the sensor surface is 20% or less of the total surface area of the shell, particularly wherein the surface area of the sensor surface is 10% or less of the total surface area of the shell, more particularly wherein the surface area of the sensor surface is 1% or less of the total surface area of the shell, most particularly wherein the surface area of the sensor surface is 0.1% or less of the total surface area of the shell.

The sensor surface can be comprised in an electrode or is a part of an electrode, wherein particularly the electrode is configured to detect a parameter related to corrosion or to the durability performance of the concrete structure, more particularly the electrode is configured to detect a parameter related to corrosion of a reinforcement bar of the concrete structure. In particular, said parameter is an electric potential, an electric resistance, an electric impedance, an electric current, more particularly a macrocell current, an electrochemical parameter related to transport processes within the concrete (e.g. ion concentrations), moisture, or a conductivity.

The term 'macrocell current' may describe an electric current that flows within a macro corrosion element between anodic and cathodic areas and used as an indication of the time to depassivation.

The sensor surface can be a piezoelectric element or is part of a piezoelectric element, wherein particularly the piezoelectric element is configured to detect stress, strain, vibrations or cracks of the concrete structure into which the sensor assembly is embedded.

The at least one sensor, particularly the sensor surface, can protrude 1 mm or less from the shell of the body. This minimizes the artifacts introduced by the material and/or shape of the sensor surface.

The mineral material comprised in the sensor shell can be a cement paste or a fine mortar.

The mineral material can have a water-to-cement ratio of 0.5 or less.

The mineral material can be a fine mortar comprising aggregates of a maximum size of 1 mm.

The sensor assembly, particularly the shell of the sensor assembly, can have a thermal conductivity of 0.5 W/(m·K) to 3 W/(m·K).

In certain embodiments, the mineral material can have a thermal conductivity of 0.5 W/(m·K) to 3 W/(m·K).

The sensor assembly, particularly the shell of the sensor assembly, can have a water absorption of 0% to 2% (percentage by mass, i.e. the mass of water absorbed divided by the mass of the sensor assembly).

The mineral material can have a water absorption of 0% to 2% (percentage by mass, i.e. the mass of water absorbed divided by the mass of the mineral material).

As used herein, the term 'water absorption' may designate the water absorption determined according to applicable standards, for example, the European Standard EN 1097-6 (Tests for mechanical and physical properties of aggregates—Part 6: Determination of particle density and water absorption).

The sensor assembly, particularly the shell of the sensor assembly, can have a water absorption in the range specified for concrete aggregates in applicable standards, for example European Standard EN 12620 (Aggregates for concrete).

The sensor assembly, particularly the shell of the sensor assembly, can have a drying shrinkage of 0.075% (percentage by mass) or less.

The mineral material can have a drying shrinkage of 0.075% (percentage by mass) or less.

As used herein, the term 'drying shrinkage' can designate the drying shrinkage determined according to applicable standards, for example, the European Standard EN 1367-4 (Tests for mechanical and physical properties of aggregates—Part 4: Determination of drying shrinkage).

The sensor assembly can have a drying shrinkage in the range specified for concrete aggregates in applicable standards, for example European Standard EN 12620 (Aggregates for concrete).

The sensor assembly can have a resistance to freezing and thawing of 50% loss of mass or less.

The mineral material can have a resistance to freezing and thawing of 50% loss of mass or less.

The term 'resistance to freezing and thawing' as used herein can refer to the resistance to freezing and thawing determined according to applicable standards, for Example European Standard EN 1367-6 (Tests for thermal and weathering properties of aggregates—Determination of resistance to freezing and thawing in the presence of salt (NaCl).

The sensor assembly can have a resistance to freezing and thawing in the range specified for concrete aggregates in applicable standards, for example European Standard EN 12620 (Aggregates for concrete).

The mineral material of the shell of the sensor assembly can display no alkali-silica reaction.

The sensor assembly can comprise a plurality of sensors, each of the sensors being configured to determine a parameter related to the durability of a concrete structure when the sensor assembly is embedded in the concrete structure.

The sensor assembly can comprises a first sensor (comprised in the above-mentioned at least one sensor) configured to determine parameters related to corrosion, corrosion risk or corrosion propagation of the concrete structure into which the sensor assembly is embedded.

The first sensor can be configured to measure an electric potential, an electric resistance, an electric current, more particularly a macrocell current, an electrochemical transport process, a moisture, a conductivity, or a temperature.

The first sensor can comprise at least one electrode configured to measure an electric potential, an electric resistance, an electric current, more particularly a macrocell current, an electrochemical transport process, a moisture, or a conductivity.

The sensor assembly can comprise a second sensor (comprised in the above-mentioned at least one sensor) configured to determine parameters related to structural health, particularly stress, strain, vibrations or cracks, of the concrete structure into which the sensor assembly is embedded.

The second sensor can be a piezoelectric sensor.

The sensor assembly can comprise a wireless communication module (e.g. a wireless transceiver) arranged inside the body (i.e. not exposed to the surface of the shell), wherein the wireless communication module is configured to transmit the parameters determined by the at least one sensor to an external communication module. To this end, the sensors are particularly electrically connected to the wireless communication module, such that data may be transferred from the respective sensor to the wireless communication module. Advantageously, the wireless communication module allows data transmission from the sensor assembly without removing the sensor assembly from the concrete structure and without using cases that could disrupt the concrete environment.

The wireless communication module can further be configured to receive signals, particularly control signals, from the external communication module.

The sensor assembly can comprise a computation device, particularly a microcomputer or an integrated circuit board, arranged inside the body (i.e. not exposed to the surface of the shell), wherein particularly the computation device is configured to control of the wireless communication module, and/or to coordinate data transmission from/to the wireless communication module, and/or perform calculations based on the parameters measured by the at least one sensor.

The sensor assembly comprises an energy source arranged inside the body (i.e. not exposed to the surface of the shell), wherein the energy source is configured to supply electric energy to the at least one sensor and/or the wireless communication module, wherein the energy source is configured to be charged wirelessly, particularly by inductive coupling. For example, the energy source may be a rechargeable or non-rechargeable battery.

The sensor assembly can comprises an inductive charging device arranged inside the body (i.e. not exposed to the surface of the shell), particularly disposed in a cavity inside the body of the sensor assembly, for inductively charging the energy source.

A second aspect of the invention relates to a reinforced or unreinforced concrete structure comprising at least one sensor assembly according to the first aspect of the invention, wherein the at least one sensor assembly is embedded in the concrete structure.

Wherever alternatives for single separable features are laid out herein as "embodiments", it is to be understood that such alternatives may be combined freely to form discrete embodiments of the invention disclosed herein.

Further scope of applicability of the present invention will become apparent from the detailed description given hereinafter. However, it should be understood that the detailed description and specific examples, while indicating preferred embodiments of the invention, are given by way of illustration only, since various changes, combinations, and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
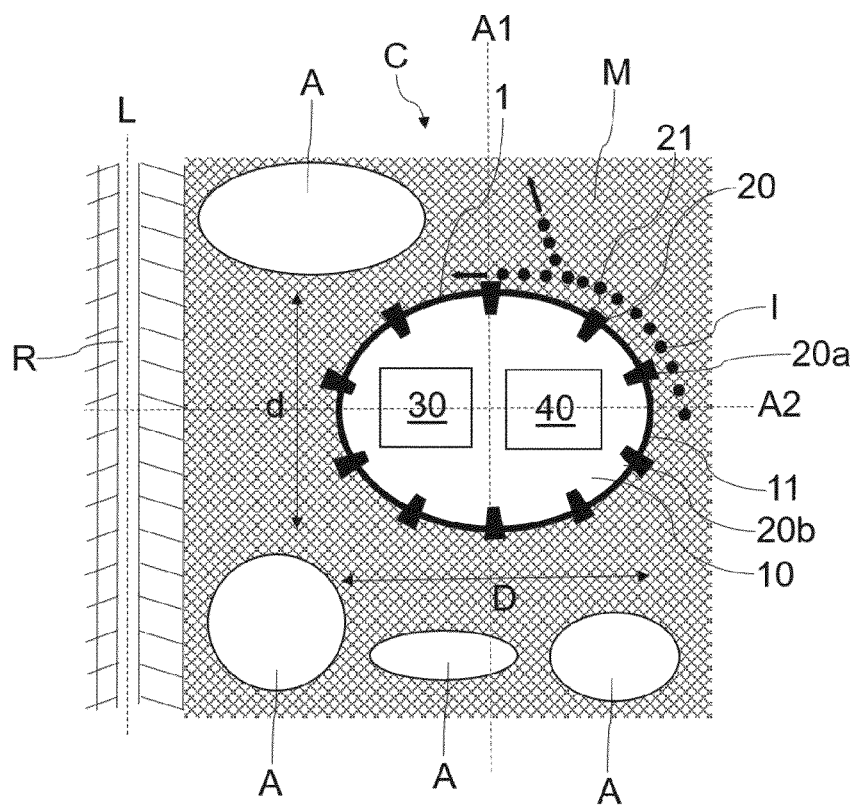
FIG. 1 shows a schematic drawing of a sensor assembly according to the invention embedded in a concrete structure.

FIG. 1 shows a cross-sectional schematic view of a concrete structure C comprising a sensor assembly 1 according to the invention. The concrete structure C comprises a cement or mortar paste M, into which aggregates A are embedded. Furthermore, the concrete structure C comprises a reinforcement bar R for mechanically reinforcing the concrete structure C. The reinforcement bar R is formed from metallic material, such as steel, and extends along a longitudinal axis L.

To monitor durability and/or structural health of the concrete structure C, a sensor assembly 1 (smart aggregate) is embedded in the concrete structure C. The sensor assembly 1 may be embedded during casting of the concrete structure C or at a later stage, e.g., by drilling a hole in the concrete structure C, inserting the sensor assembly 1 into the hole, and filling the hole with filling mortar. The sensor assembly 1 comprises a body 10 and a shell 11 forming the outer surface of the body 10 which is in contact with the surrounding concrete structure C. The shell 11 is particularly formed to at least 90% (weight to weight) from a mineral material such as a cement paste or fine mortar to reduce disturbance of the surrounding concrete structure C. Of course, it is also possible that other parts of the body 10 than the shell 11 are formed from a mineral material, particularly from the same material as the shell 11. The body 10 may comprise a cavity or several cavities to accommodate additional components such as sensors 20, energy source 40, or wireless communication module 30 (see below).

To avoid disturbance of the concrete structure C the sensor assembly 1 has a rounded, particularly spherical, or ellipsoid, shape, similar to the aggregates A disposed in the concrete structure C. The sensor assembly 1 has a first extension or height d extending along a first axis A1 which is parallel to the longitudinal axis L of the reinforcement bar R and a width D extending along a second axis A2 perpendicular to the first axis A1, wherein the ratio between the first extension d and the width D is 1:3 to 3:1. The first extension d of the sensor assembly 1 is 90 mm or smaller to ensure that the sensor assembly 1 has a similar size to the aggregates A allowed in concrete according to, for example, European standard EN 12620.

Furthermore, the sensor assembly 1 comprises a plurality of sensors 20, 20a, 20b, which are partially disposed inside of the body 10 and comprise a sensor surface 21 arranged on the outside of the shell 11. The sensors 20, 20a, 20b are protruding from the shell 11, particularly by a distance of 1 mm or less (measured in a radial direction perpendicular to the surface of the shell 11).

For example, the sensor 20a may be configured for durability monitoring, in other words, to detect corrosion, corrosion risk or corrosion propagation or ingress I of species (e.g., ions), liquid or gases (see FIG. 1). To this end, the sensor 20a may comprise an electrode or a plurality of electrodes to measure one of the following parameters:

an electrical impedance (resistance) of the concrete structure, measured between different electrodes, wherein the sensor particularly comprises these electrodes of a corrosion-resistant metal alloy or mixed metal-metal oxides;

a macrocell electric current, in other words, an electric current that flows within a macro-corrosion element between anodic and cathodic areas and used as an indication of the time to depassivation, wherein particularly the sensor may comprise an array of steel electrodes mounted at different depths from the concrete surface, between which macro-cells are established;

parameters related to transport processes, in particular a measurement of chloride, pH, and moisture profiles, e.g., by measurement of Ag/AgCl ion-selective electrodes and iridium/iridium oxide electrodes, respectively, versus a reference electrode; chloride and pH sensors may be formed of thin wires made of metallic materials; for moisture monitoring purposes hygrometric sensors may be used.

For example, the second sensor 20b shown in FIG. 1 may be configured to monitor the structural health of the concrete structure C, in other words, stress, strain, vibrations or cracks. To this end, the second sensor 20b may comprise a piezoelectric element capable of converting mechanical strain to an electric signal.

The sensor assembly 1 may further comprise a wireless communication module 30, particularly a wireless transceiver, for transmitting parameters measured by the sensors 20, 20a, 20b to an external receiver of the wireless signal. The wireless communication module 30 may be disposed in a cavity inside the body 10 of the sensor assembly 1. In addition to transmitting data, the wireless communication module 30 may also be configured to receive control signals from an external source. Any suitable communication standard may be used to transmit the measured parameters and/or receive control signals.

In particular, for control of the wireless communication module 30, coordination of data transmission, optional calculations based on the measured parameters or other control operations, the sensor assembly 1 may comprise a microcomputer or an integrated circuit board (not shown in FIG. 1).

Furthermore, the sensor assembly 1 may comprise an electric energy source 40, such as a battery, to provide electrical energy to the sensors 20, 20a, 20b and/or to operate the wireless communication module 30. In particular, the energy source 40 may be configured to be charged by inductive coupling, such that the energy source 40 may be remotely charged without removing the sensor assembly 1 from the concrete structure C. To this end, the sensor assembly 1 may comprise an inductive charging device, particularly disposed in a cavity inside the body 10 of the sensor assembly 1.

Figure 2:
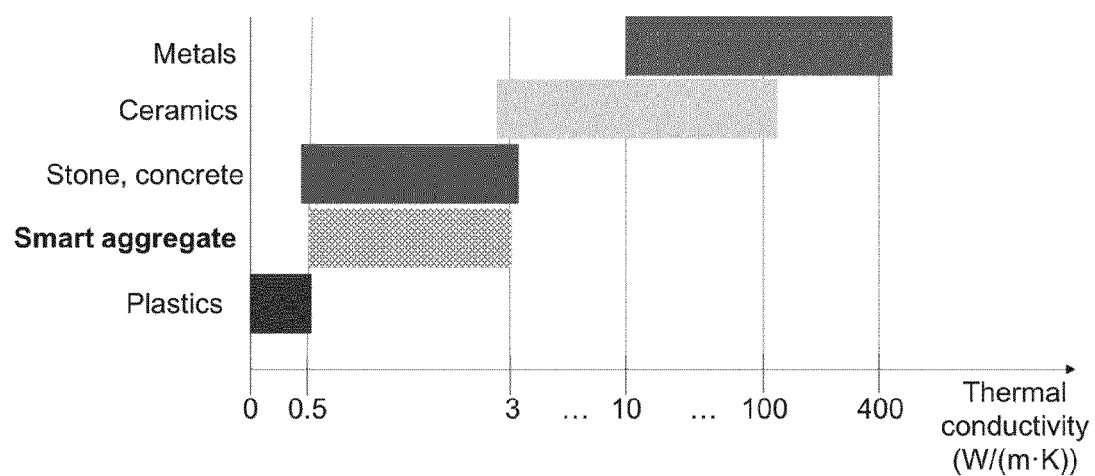
FIG. 2 shows thermal conductivity ranges of different materials compared to the thermal conductivity range of the sensor assembly according to the invention.

FIG. 2 shows a comparison of thermal conductivity values of different materials with the sensor assembly 1 according to the present invention ("smart aggregate"). The thermal conductivity values of material of the shell 11 are similar to those of stone and concrete and therefore minimize artifacts (such as induction of corrosion) induced by the sensor assembly 1.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A sensor assembly for determining parameters related to a durability of a concrete structure, the sensor assembly comprising:
    a body; and
    at least one sensor configured to determine at least one parameter related to the durability of the concrete structure when the sensor assembly is embedded in the concrete structure, the at least one sensor being arranged at least partially within the body,
    wherein the body comprises a shell that covers an outer surface of the body,
    wherein at least 90% of the shell consists of or comprises a mineral material, the mineral material being a cement paste or a fine mortar,
    wherein the sensor assembly or the shell has an ellipsoid shape or a spherical shape,
    wherein the sensor assembly or the shell comprises a first extension extending along a first axis, the first extension being 90 mm or less,
    wherein the sensor assembly comprises a first sensor configured to determine parameters related to corrosion, corrosion risk or corrosion propagation of the concrete structure into which the sensor assembly is embedded, and
    wherein the first sensor is configured to measure an electrochemical transport process.

2. The sensor assembly according to claim 1, wherein the sensor assembly or the shell comprises a second extension extending along a second axis substantially perpendicular to the first axis, and wherein a ratio between the second extension and the first extension is 1:3 to 3:1.

3. The sensor assembly according to claim 1, wherein the at least one sensor comprises a sensor surface formed by the at least one sensor, wherein the sensor surface is disposed on an outside surface of the shell of the sensor assembly such that the sensor surface is configured to contact the concrete structure adjacent the sensor assembly when the sensor assembly is embedded in the concrete structure.

4. The sensor assembly according to claim 3, wherein a surface area of the sensor surface is 20% or less of a total surface area of the shell or wherein the surface area of the sensor surface is 10% or less of the total surface area of the shell.

5. The sensor assembly according to claim 3, wherein the at least one sensor or the sensor surface protrudes 1 mm or less from the shell of the body.

6. The sensor assembly according to claim 1, wherein the sensor assembly has a thermal conductivity of 0.5 W/(m·K) to 3 W/(m·K).

7. The sensor assembly according to claim 1, wherein the sensor assembly has a water absorption of 0% to 2%.

8. The sensor assembly according to claim 1, wherein the sensor assembly has a drying shrinkage of 0.075% or less.

9. The sensor assembly according to claim 1, wherein the sensor assembly has a resistance to freezing and thawing of 50% loss of mass or less.

10. The sensor assembly according to claim 1, wherein the first sensor is further configured to measure an electric potential, an electrical impedance, an electric current, a macrocell current, a moisture, a conductivity or a temperature, and wherein the first sensor comprises at least one electrode.

11. The sensor assembly according to claim 1, wherein the sensor assembly comprises a second sensor or a piezoelectric sensor configured to determine at least one parameter related to structural health, stress, strain, vibrations or cracks of the concrete structure into which the sensor assembly is embedded.

12. The sensor assembly according to claim 1, wherein the sensor assembly comprises a wireless communication module configured to transmit the at least one parameter determined by the at least one sensor to an external communication module.

13. The sensor assembly according to claim 12, wherein the sensor assembly comprises an energy source configured to supply electric energy to the at least one sensor and/or the wireless communication module, and wherein the energy source is configured to be charged wirelessly or by inductive coupling.

14. A concrete structure comprising at least one of the sensor assembly according to claim 1, wherein the at least one of the sensor assembly is embedded in the concrete structure.

* * * * *